US006394088B1

(12) United States Patent
Frye et al.

(10) Patent No.: US 6,394,088 B1
(45) Date of Patent: May 28, 2002

(54) OXYGEN-DELIVERY SYSTEM WITH PORTABLE OXYGEN METER

(76) Inventors: Mark R. Frye, 3735 N. Birdie Galyan Rd., Bloomington, IN (US) 47408; J. Fred Brown, 9443 Lowell St., Overland Park, KS (US) 66212; Douglas R. Leithauser, 441 Tulip Popular Crest, Carmel, IN (US) 46033

( * ) Notice: Subject to any disclaimer, the term of this patent is extended or adjusted under 35 U.S.C. 154(b) by 0 days.

(21) Appl. No.: 09/435,174

(22) Filed: Nov. 5, 1999

Related U.S. Application Data

(60) Provisional application No. 60/107,456, filed on Nov. 6, 1998.

(51) Int. Cl.⁷ .............................................. A61M 16/00
(52) U.S. Cl. ........................... 128/204.26; 128/204.23; 128/205.24
(58) Field of Search ...................... 128/205.22, 207.18, 128/204.23, 204.26, 205.24, 202.27, 912

(56) References Cited

U.S. PATENT DOCUMENTS

| 2,144,611 | A | * | 1/1939 | Biggs | 128/141 |
| 2,573,414 | A | * | 10/1951 | Dunn | 128/144 |
| 2,700,535 | A | * | 1/1955 | Harrington et al. | 259/151 |

(List continued on next page.)

FOREIGN PATENT DOCUMENTS

| WO | WO97/11734 | 4/1997 |

OTHER PUBLICATIONS

DeVilbiss PulseDose™ Oxygen Management System 50 Instruction Guide (1995; Copy of cover page and pp. 2–20).
DeVilbiss EX2000D PulseDose™ Conserving Device Instruction Guide (1997; Copy of cover page and pp. 2–16).
O₂ Advantage® Model CD1 Product Information and Operating Instructions [Apr. 1, 1997; Copy of cover page, Table of Contents, pp. 1–29; Photographic images of cover page and product disclosed therein (photos 1–2)].
ImPulse™ OCD System Patient Manuel [Oct. 1996; Copy of cover page, Table of Contents, and pp. 1–26; Photographic images of cover page and product disclosed therein (photos 3–4)].
Prior art Chad Model 2400 Oxymatic® Electronic Oxygen Conserver System Product Information and Instructions for Use [Copy of cover page and pp. 2–19; Photographic images of cover page and product disclosed therein (photos 5–6)].
Invacare® Venture™ Demand Oxygen Delivery Device and System Operator's Manual (Jan. 1996; Copy of cover page, pp. 2–23, and back cover).

*Primary Examiner*—John G. Weiss
*Assistant Examiner*—Mital Patel
(74) *Attorney, Agent, or Firm*—Barnes & Thornburg

(57) ABSTRACT

An oxygen-delivery system comprises a portable oxygen meter including a low-pressure oxygen inlet, a low-pressure oxygen outlet, and an exhale-inhale sensing port, an oxygen-supply source including a discharge outlet and configured to discharge low-pressure oxygen through the discharge outlet, a flexible supply tube arranged to conduct low-pressure oxygen from the oxygen-supply source into the portable oxygen meter through the low-pressure oxygen inlet, and a nasal cannula coupled to the low-pressure oxygen outlet and the exhale-inhale sensing port. The portable oxygen meter further includes a pneumatic demand oxygen conserver including a diaphragm valve member, control means coupled to the exhale-inhale sensing port for causing the diaphragm valve member to move to a flow-delivery position in response to inhalation of a patient and to a flow-blocking position in response to a lack of inhalation by the patient during exhalation through the nasal cannula, and an oxygen flow passage arranged to pass low-pressure oxygen through an oxygen flow-metering aperture to meter low-pressure oxygen outlet at a selected oxygen flow rate. The oxygen-delivery system further comprises a mount including a flange coupled to the portable oxygen meter and a clip adapted to be coupled to an item of clothing worn by the patient.

26 Claims, 9 Drawing Sheets

U.S. PATENT DOCUMENTS

| | | | | |
|---|---|---|---|---|
| 3,291,126 A | * | 12/1966 | Messick | 128/142.4 |
| 3,777,750 A | * | 12/1973 | Savornin | 128/142.5 |
| 4,054,133 A | * | 10/1977 | Myers | 128/142.2 |
| 4,271,833 A | * | 6/1981 | Moretti | 128/201.29 |
| 4,304,224 A | * | 12/1981 | Fortney | 128/1 R |
| 4,413,622 A | * | 11/1983 | Austin | 128/205.25 |
| 4,575,042 A | * | 3/1986 | Grimland et al. | 251/46 |
| 4,794,922 A | * | 1/1989 | DeVries | 128/204.18 |
| 4,827,921 A | * | 5/1989 | Rugheimer | 128/202.27 |
| 4,883,051 A | * | 11/1989 | Westenskow et al. | 128/204.21 |
| 4,989,599 A | * | 2/1991 | Carter | 128/207.18 |
| 5,027,807 A | * | 7/1991 | Wise et al. | 128/201.28 |
| 5,099,836 A | * | 3/1992 | Rowland et al. | 128/204.23 |
| 5,134,886 A | | 8/1992 | Ball | |
| 5,137,017 A | * | 8/1992 | Salter | 128/207.18 |
| 5,165,397 A | * | 11/1992 | Arp | 128/204.21 |
| 5,181,508 A | * | 1/1993 | Poole, Jr. | 128/203.12 |
| 5,280,780 A | * | 1/1994 | Abel | 128/203.14 |
| 5,293,864 A | * | 3/1994 | McFadden | 128/201.29 |
| 5,360,000 A | * | 11/1994 | Carter | 128/204.26 |
| 5,443,062 A | * | 8/1995 | Hayes | 128/204.26 |
| 5,472,317 A | * | 12/1995 | Field et al. | 417/234 |
| 5,603,315 A | * | 2/1997 | Sasso, Jr. | 128/204.18 |
| 5,666,945 A | * | 9/1997 | Davenport | 128/200.14 |
| 5,678,542 A | * | 10/1997 | Maffatone | 128/205.24 |
| 5,755,224 A | * | 5/1998 | Good et al. | 128/205.24 |
| 5,865,174 A | * | 2/1999 | Kloeppel | 128/204.23 |
| 5,881,725 A | * | 3/1999 | Hoffman et al. | 128/204.26 |
| 6,026,810 A | * | 2/2000 | Baird | 128/207.14 |
| 6,116,242 A | * | 9/2000 | Frye et al. | 128/205.24 |

* cited by examiner

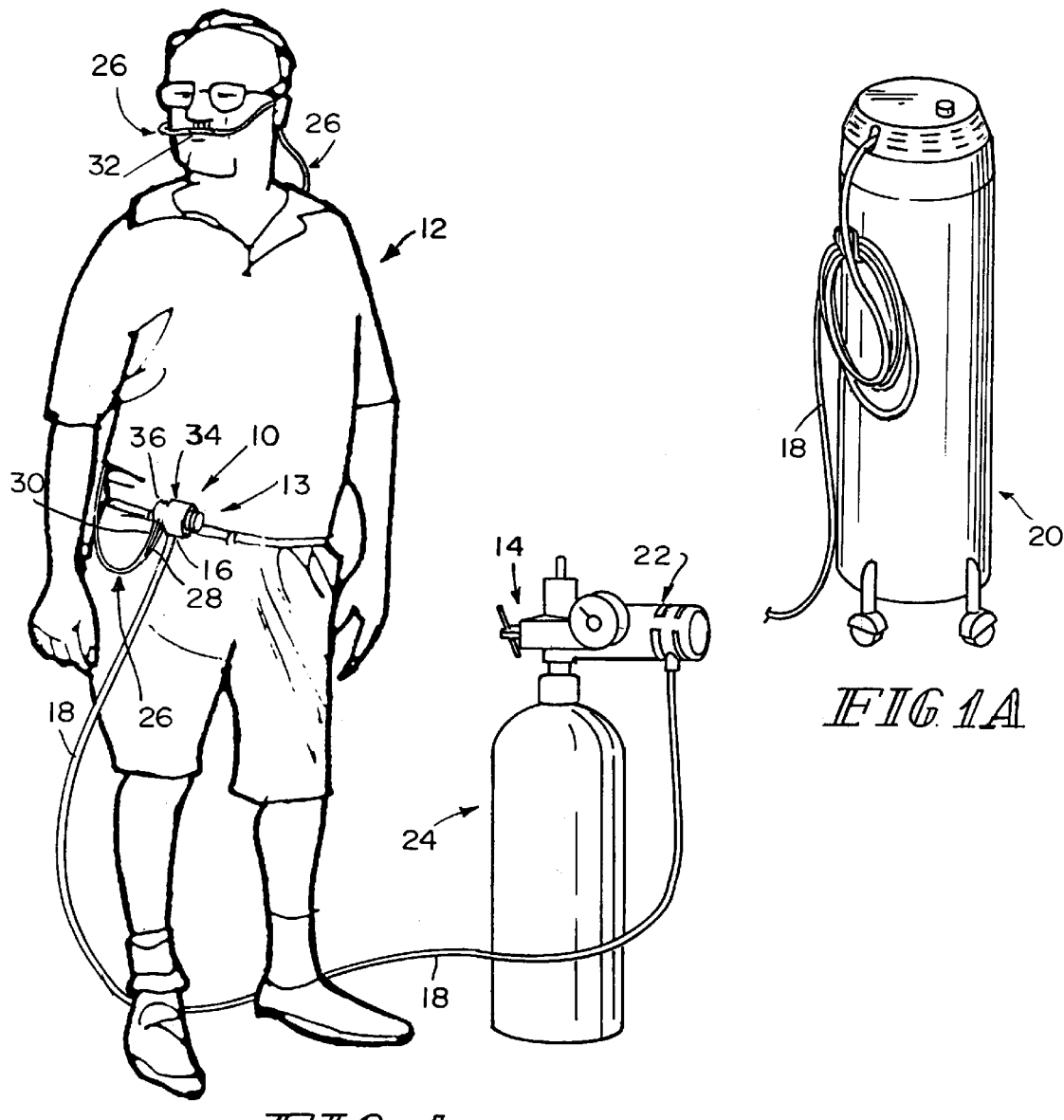
FIG. 1
FIG. 1A
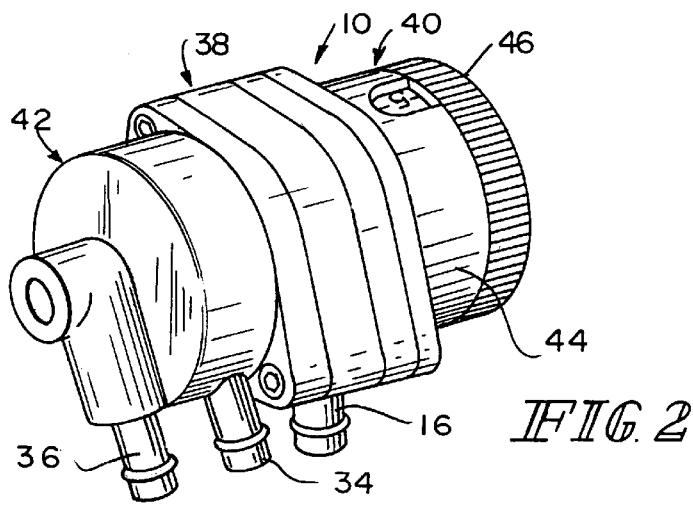
FIG. 2

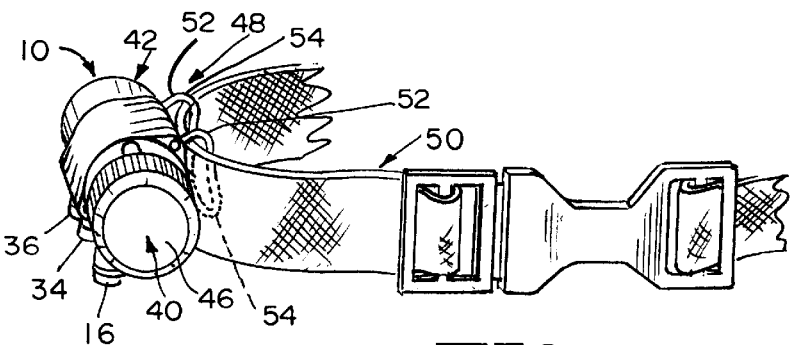
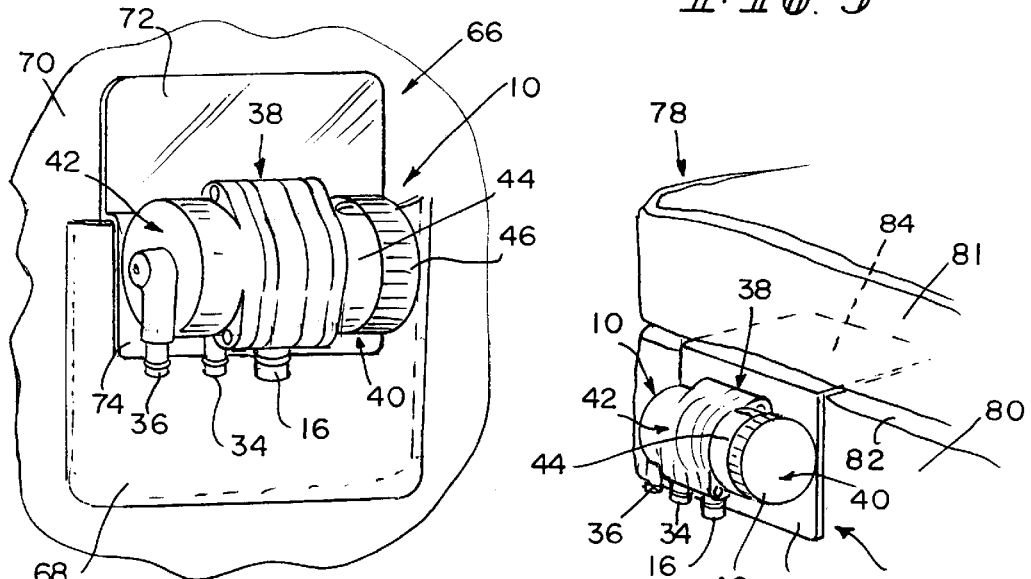
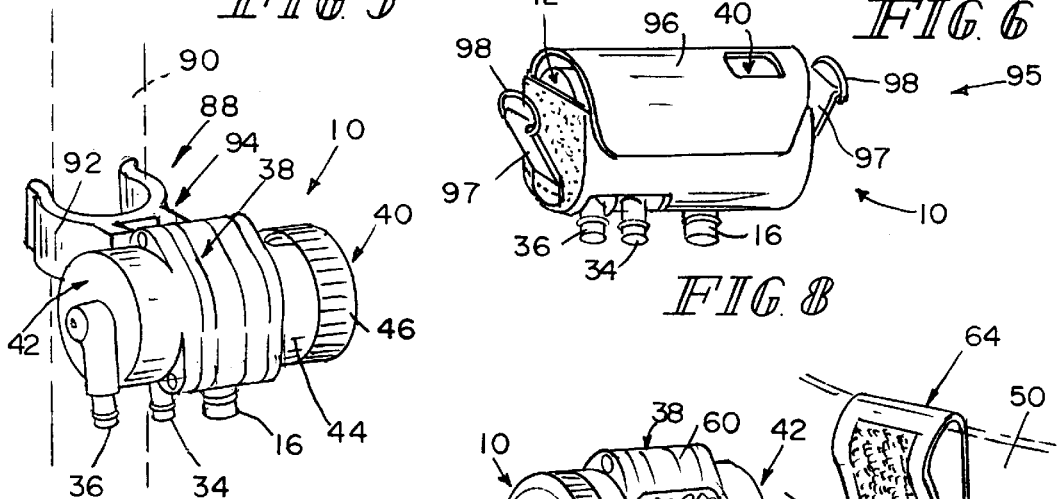
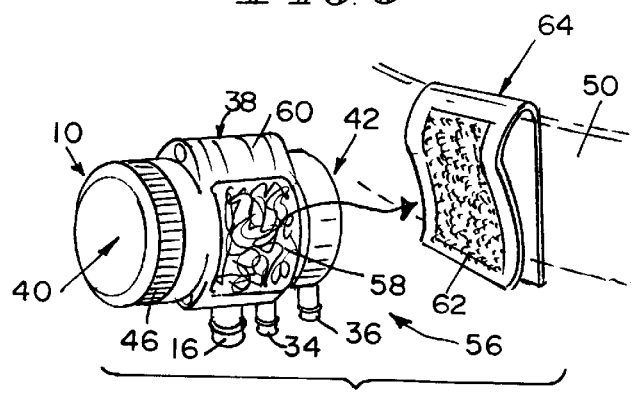

OXYGEN-DELIVERY SYSTEM WITH PORTABLE OXYGEN METER

This application claims priority under 35 U.S.C. 119(e) to U.S. Provisional Application Ser. No. 60/107,456, filed Nov. 6, 1998, which is expressly incorporated by reference herein.

BACKGROUND AND SUMMARY OF THE INVENTION

The present invention relates to systems for delivering oxygen to patients undergoing respiratory therapy, and particularly to oxygen-delivery systems including an oxygen meter. More particularly, the present invention relates to a portable oxygen meter for use with an oxygen-delivery system.

Supplemental oxygen-delivery systems are provided to administer medicinal gas, normally oxygen, to a patient undergoing respiratory therapy. Supplemental oxygen-delivery systems are used by patients that benefit from receiving and breathing oxygen from an oxygen supply source to supplement atmospheric oxygen breathed by the patients. A compact, portable supplemental oxygen-delivery system is useful in a wide variety of contexts, including hospital, home care, and ambulatory settings.

High-pressure supplemental oxygen-delivery systems typically include a cylinder or tank containing oxygen gas at a pressure of up to 3000 psig. A pressure regulator is used in a high-pressure oxygen-delivery system to "step down" the pressure of oxygen gas in the tank to a lower pressure level (e.g., 20 or 50 psig) suitable for use in an oxygen-delivery apparatus used by a patient in respiratory therapy.

According to the present invention, an oxygen-delivery system includes a low-pressure oxygen supply, a portable oxygen meter including a pneumatic demand oxygen conserver, a flexible supply tube to conduct low-pressure oxygen from the low-pressure oxygen supply to the portable oxygen meter, and a nasal cannula coupled to the portable oxygen meter and adapted to be inserted into the nasal cavities of a patent. The portable oxygen meter operates to meter low-pressure oxygen flowing therethrough so that the low-pressure oxygen is discharged from the portable oxygen meter to a patient through the nasal cannula at a selected oxygen flow rate.

In preferred embodiments, the portable oxygen meter includes a manifold formed to include a low-pressure oxygen inlet coupled to an outlet end of the flexible supply tube to receive low-pressure oxygen flowing through the tube, and a flow controller module mounted on one side of the manifold. The pneumatic demand oxygen conserver is contained in a module mounted on an opposite side of the manifold and coupled to the nasal cannula.

Low-pressure oxygen is discharged from the flexible supply tube into the manifold and the oxygen is passed through one of several oxygen flow-metering apertures (of varying sizes) located in the flow controller module to regulate and set the flow rate of low-pressure oxygen (measured in liters per minute) that is conducted from the flow controller module (back through the manifold) to the pneumatic demand oxygen conserver for distribution to a patient via the nasal cannula. The pneumatic demand oxygen conserver functions to take metered, low-pressure oxygen from the flow-controller module and distribute it to a patient at various times in response to inhalation of the patient through the nasal cannula.

Low-pressure oxygen is discharged into the inlet end of the flexible supply tube from a low-pressure supply of liquid oxygen or from a tank containing high-pressure oxygen and a pressure regulator configured to "step down" the pressure of oxygen in the tank to a lower pressure level. The length of the flexible supply tube can be fairly long (e.g., over twenty feet) to enhance the portability of the portable oxygen meter.

A meter mount is coupled to the manifold and adapted to be worn by a patient to minimize the length of the nasal cannula that carries metered, low-pressure oxygen from the portable oxygen meter to the patient. The meter mount includes lugs that fit into notches formed in the manifold and a clip adapted to be coupled to a belt worn by the patient. Other meter mounts are also disclosed herein.

Additional features of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 1 is a perspective view of an oxygen delivery system in accordance with the present invention showing a patient wearing a portable oxygen meter on his belt, a flexible supply tube conducting low-pressure oxygen discharged from a pressure regulator mounted on top of a high-pressure oxygen tank to a low-pressure oxygen inlet in the portable oxygen meter, and a patient breathing cannula worn by the patient and coupled to a low-pressure oxygen outlet and an exhale/inhale sensor port in the portable oxygen meter;

FIG. 1A is a perspective view of a low-pressure liquid oxygen tank coupled to the flexible supply tube;

FIG. 2 is an enlarged perspective view of the portable oxygen meter of FIG. 1 showing a left-side pneumatic demand oxygen conserver module formed to include the low-pressure oxygen outlet and the exhale/inhale sensor port, a right-side oxygen flow controller module, and a manifold positioned to lie between the oxygen conserver and flow controller modules and formed to include the low-pressure oxygen inlet;

FIG. 3 is a perspective view of the portable oxygen meter of FIG. 2 clipped to a belt;

FIG. 4 is a perspective view of the portable oxygen meter of FIG. 2 provided with a hook-and-loop connector so that it can be coupled to a matching hook-and-loop connector on a belt clamp;

FIG. 5 is a perspective view of the portable oxygen meter of FIG. 2 coupled to a pocket-protector mount;

FIG. 6 is a perspective view of the portable oxygen meter of FIG. 2 coupled to a bed/mattress or overstuffed chair or sofa mount;

FIG. 7 is a perspective view of the portable oxygen meter of FIG. 2 coupled to a clamp mount that is configured to grip a walker or wheel chair post;

FIG. 8 is a perspective view of the portable oxygen meter of FIG. 2 contained in a pouch mount that is configured to be slung on a strap passing through rings attached to a pouch;

DETAILED DESCRIPTION OF THE DRAWINGS

Figure 9:
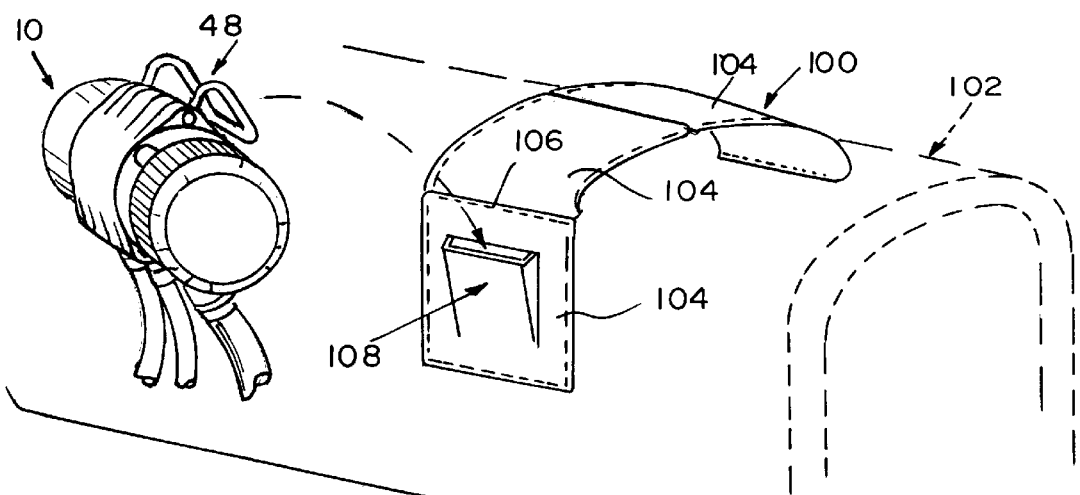
FIG. 9 is a perspective view of the portable oxygen meter of FIG. 2 adapted to be mounted in a pocket formed in a weighted, segmented anchor mount sized to stay on the arm of a chair, sofa, or other base.

A portable oxygen meter 10 is adapted to be worn or carried by a patient 12 and to supply oxygen in a measured or regulated amount to the patient 12 as shown, for example, in FIG. 1. Oxygen meter 10 functions as a patient breathing assist apparatus to receive low-pressure oxygen from a supply source and distribute low-pressure oxygen to a patient in need of oxygen at a flow rate, timing, and mode of delivery (e.g., on-demand flow or continuous flow). The portability of oxygen meter 10 maximizes mobility of a patient receiving oxygen through oxygen meter 10.

Oxygen supply 14 is coupled to an oxygen inlet 16 in oxygen meter 10 by a flexible supply tube 18 configured to conduct low-pressure oxygen from oxygen supply 14 to oxygen meter 10. Oxygen supply 14 includes a high-pressure oxygen tank 24 and a pressure regulator 22 mounted on the high-pressure oxygen tank 24 as shown, for example, in FIG. 1. Pressure regulator 22 functions to convert high-pressure oxygen discharged from oxygen tank 24 into low-pressure oxygen (e.g., about 20 pounds per square inch) suitable for use by a patient undergoing oxygen therapy. In an alternative embodiment shown in FIG. 1A, flexible supply tube 18 can be coupled to a low-pressure oxygen tank 20 configured to include a low-pressure supply of liquid oxygen (e.g., about 20 pounds per square inch).

The low-pressure oxygen is discharged from tank 24 into flexible supply tube 18 for delivery to portable oxygen meter 10 as suggested in FIG. 1. The length of supply tube 18 can be increased to extend the range a patient carrying portable oxygen meter 10 may roam away from oxygen tank 24 and yet receive low-pressure oxygen supplied by oxygen tank 24. Tube sections can be linked together to form a long supply tube 18. A presently preferred oxygen delivery system 211 including portable oxygen meter 10 is shown diagrammatically in FIG. 12.

As shown in FIG. 1, a nasal cannula 26 is coupled to oxygen meter 10 and adapted to be inserted into the nasal cavities of patient 12. Regardless of the length of oxygen supply tube 18, the length of cannula is relatively short as it must only be long enough to extend between the patient 12 and the portable oxygen meter 10 adjacent to the patient 12. The patient's mobility range away from oxygen supply 14 is limited by the length of oxygen supply tube 18 and not the length of nasal cannula 26.

In the illustrated embodiment, nasal cannula 26 is a dual lumen cannula including a gas supply tube 28, a breath sensor tube 30, and a nasal delivery structure 32. Dual lumen cannula 26 is illustrated in greater detail in FIG. 17 and a more detailed description of nasal cannula 26 is provided later in this disclosure. Gas supply tube 28 is coupled to a low-pressure oxygen outlet 34 in oxygen meter 10 and breath sensor tube 30 is coupled to sensor port 36 in oxygen meter 10. Portable oxygen meter 10 is quite responsive to the oxygen needs of patient 12 due to the relatively short length of nasal cannula 26.

In use, whenever a patient wearing nasal cannula 26 and carrying portable oxygen meter 10 placed in "demand mode" (e.g., adapted to provide on-demand oxygen flow to a patient) inhales, low-pressure oxygen delivered through flexible supply tube 18 to oxygen meter 10 is delivered from oxygen meter 10 to patient 12 through gas supply tube 28 and nasal delivery structure 32 in nasal cannula 26. Whenever the same patient 12 exhales, exhaled air is discharged into nasal delivery structure 32 and through breath sensor tube 30. The lack of inhalation by a patient during exhalation causes low-pressure oxygen in oxygen meter 10 to stop flowing into gas supply tube 28 and thus temporarily suspend the flow of low-pressure oxygen to patient 12 through gas supply tube 28.

Because the lengths of gas supply tube 28 and breath sensor tube 30 in nasal cannula 26 are short, e.g., less than 7 feet (2.13 meters), oxygen meter 10 can be operated in demand mode at a distance of more than 50 feet (15.24 meters) from oxygen supply 14 without signal and delivery "distortion" (i.e., significant delay in gas delivery response time to patient). Portable oxygen meter 10 enables patient 12 to move about while maintaining the ability to receive a conserved oxygen delivery without the signal and delivery distortion caused by moving gas through a long length of tubing. Oxygen meter 10 is also adaptable to operate in "continuous mode" so as to provide continuous oxygen flow to patient 12 rather than the on-demand oxygen flow just described.

Figure 12:
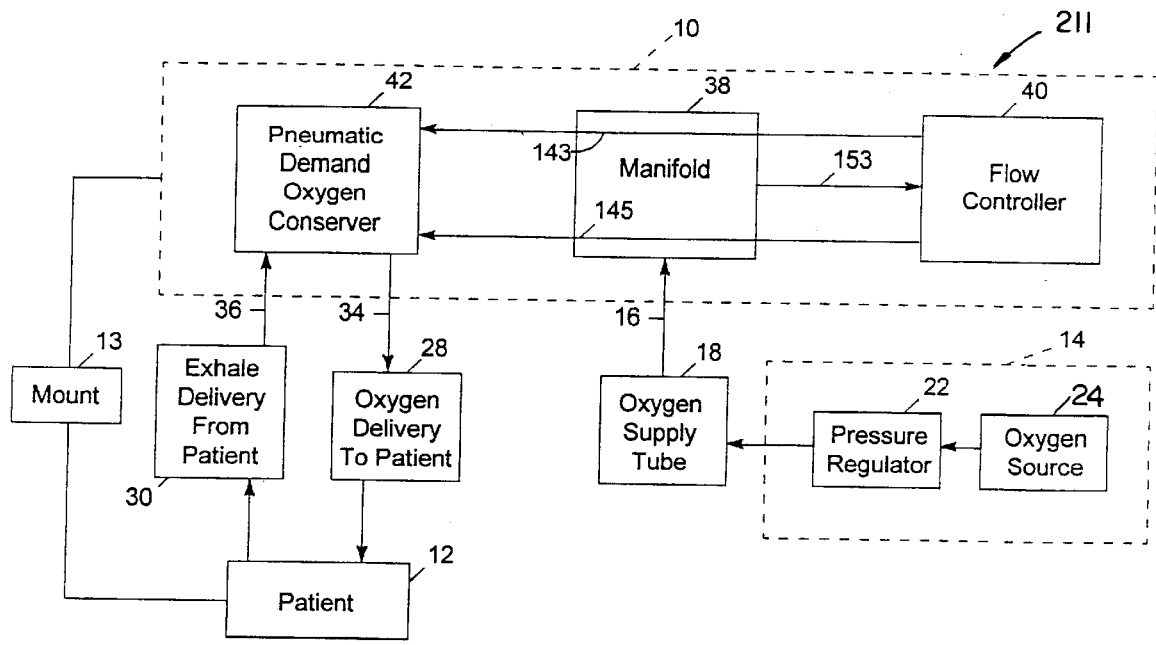
FIG. 12 is a diagrammatic view of one oxygen delivery system in accordance with the present invention showing an oxygen supply tube coupled to a manifold included in an oxygen meter having a pneumatic demand oxygen conserver and a flow controller.

Referring now to FIGS. 2 and 12, oxygen meter 10 includes a manifold 38, a flow controller 40, and a pneumatic demand oxygen conserver 42. Manifold 38 includes low-pressure oxygen inlet 16 and is positioned to lie between flow controller 40 and oxygen conserver 42. Oxygen conserver 42 includes low-pressure oxygen outlet 34 and sensor port 36. Flow controller 40 functions to meter low-pressure oxygen passing from supply tube 18 into flow controller 40 through manifold 38 at a certain flow rate (typically measured in liters per minute) and discharge that metered low-pressure oxygen into manifold 38 for delivery to oxygen conserver 42. Flow controller 40 includes a base 44 coupled to manifold 38 and a flow selector knob 46 movable relative to base 44 to change the flow rate of low-pressure oxygen discharged from flow controller 40. Oxygen conserver 42 functions to take low-pressure, metered oxygen from flow controller 40 and distribute it to a patient 12 at various times in response to inhalation of patient 12 through the cannula 26 worn by patient 12.

Apparatus configured to enable patient 12 to wear or carry portable oxygen meter 10 easily as patient 12 roams relative to oxygen tank 24 are illustrated in FIGS. 3–11. Descriptions of various mounts 13 for oxygen meter 10 are provided in the following paragraphs.

A belt clip 48 is configured to enable patient 12 to clip oxygen meter 10 to a belt 50 worn by patient 12 as shown, for example, in FIG. 3. Belt clip 48 includes a connector 52 coupled to a portion of oxygen meter 10 and clip hardware 54 fixed to connector 52 and arranged to hook onto belt 50. A presently preferred belt clip 248 on a portable oxygen meter 210 is shown in FIGS. 18–21. Manifold 38 in oxygen meter 210 is formed to include two lug-receiving notches 212, 213 in a perimeter wall 214 of manifold 38. Belt clip 248 includes a mounting flange 215 and a clip 220 appended to flange 215. The mounting flange 215 includes a top wall 216 carrying a first lug 218 sized to fit into lug-receiving notch 212 in manifold 38 and a side wall 217 carrying a second lug 219 sized to fit into lug-receiving notch 213 in manifold 38. Side wall 217 is oriented to lie in nearly perpendicular relation to top wall 216.

A hook-and-loop connector 56 is configured to enable patient 12 to couple oxygen meter to to a belt 50 worn by patient 12 as shown, for example, in FIG. 4. A first portion 58 of connector 56 is fixed to a strap 60 wrapped around a portion of oxygen meter 10. A second portion 62 of connector 56 is configured to mate with first portion 58 and is fixed to a clasp 64 hooked onto belt 50.

A pocket-protector mount 66 is configured to enable patient 12 to couple oxygen meter 10 to a pocket 68 formed on a piece of clothing 70 worn by patient 12 as shown, for example, in FIG. 5. Pocket-protector mount 66 includes a sheet 72 sized to fit into pocket 68 and a flap 74 appended to sheet 72 and arranged to lie in front of pocket 68 and carry oxygen meter 10 thereon. Oxygen meter 10 is coupled to flap 74.

A furniture mount 76 is configured to enable patient 12 to couple oxygen meter 10 to furniture 78 as shown, for example, in FIG. 6. Furniture 78 includes a first part 80, a second part 81, and a space 82 therebetween. Furniture 78 could be, for example, a sofa or chair with a separate cushion on a base or a bed with a mattress on a box spring. Furniture mount 76 includes a plate 84 sized to fit between first and second parts 80, 81 of furniture 78 and a flange 86 appended to plate 84 and arranged to hang downwardly in front of first part 80. Oxygen meter 10 is coupled to flange 86.

A clamp mount 88 is configured to enable patient 12 to couple oxygen meter 10 to a fixture 90 such as a pipe, tube, chair rail, bed rail, or other member adjacent to patient 12 as shown, for example, in FIG. 7. Clamp mount 88 includes a clamp 92 and a support 94 coupled to clamp 92 and to oxygen meter 10.

A pouch mount 95 is configured to enable patient 12 to couple oxygen meter 10 to a chain (not shown) or other article worn by patient 12 and is shown, for example, in FIG. 8. Pouch mount 95 includes a sleeve 96 wrapped around oxygen meter 10 and formed to include windows therein to view and expose various portions of oxygen meter 10 and support straps 97 and rings 98 for hanging sleeve 96 from a chain or other article.

An anchor mount 100 is configured to enable a patient 12 to couple oxygen meter 10 to the arm or back of a chair, sofa, other piece of furniture, or other base. Anchor mount 100 is placed on an arm 102 of a chair as shown in FIG. 9. Anchor mount 100 includes two or more segments 104 arranged in series and filled with weighted material (not shown). A hinge 106 connects each pair of adjacent segments 104 as shown, for example, in FIG. 9. A pocket 108 sized to receive the clip 48 on oxygen meter 10 is provided on, for example, one of the segments 104. Anchor mount 100 is made of a soft flexible material such as cloth or plastic sheeting and pellets provide the weighted material. Alternatively, anchor mount could be made of one or more segments that can be deformed to fit on an arm or presized to fit on an arm or can be deformable to fit or an arm or other base.

Figure 10:
FIG. 10 is a perspective view of the portable oxygen meter of FIG. 2 placed in a channel formed in meter-support mount sized to set on a table, floor, or other surface.

A meter-support mount 110 is configured to enable a patient 12 to support oxygen meter 10 above a table, floor, or other surface. Meter-support mount 110 is placed on a tabletop 112 as shown in FIG. 10. Meter-support mount 110 includes a base 114 formed to include a channel 118 sized to receive oxygen meter 10 and a friction pad 116 adhered to the underside of base 114. Base 114 has a hemispherical shape or other suitable shape. Base 114 can be made of a heavy material or filled with a heavy material to limit movement of meter-support mount 110 relative to tabletop 112. A handle 120 is appended to base 114 to enable a user to move meter-support mount 110 easily.

Figure 11:
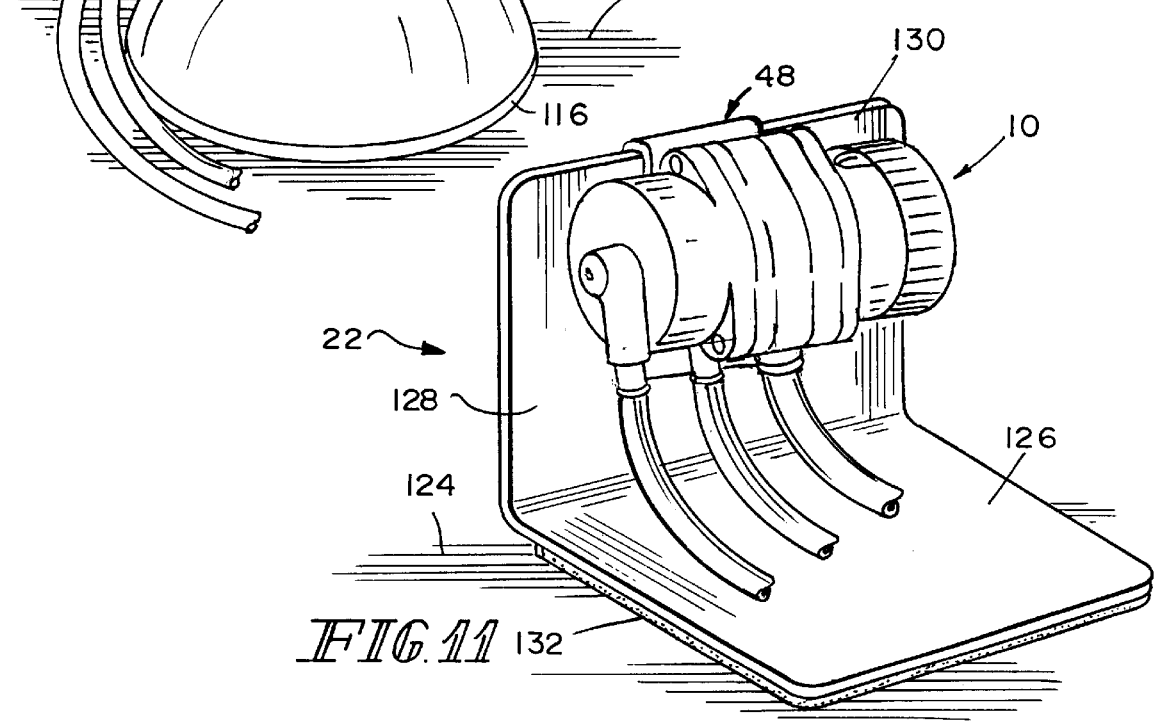
FIG. 11 is a perspective view of the portable oxygen meter of FIG. 2 clipped to an upstanding flange in a meter-support mount sized to set on a table, floor, or other surface.

Another meter-support mount 122 is configured to enable a patient 12 to support oxygen meter 10 above a table, floor, or other surface. Meter-support mount 122 is placed on a tabletop 124 as shown in FIG. 11. Meter-support mount 122 includes a base 126 and an upright flange 128 appended to base 126 and sized to receive an upper edge 130. Clip 48 engages upper edge 130 of upright flange 128 to support oxygen meter 10 on meter-support mount 122. A friction pad 132 is adhered to the underside of base 126.

Figure 17:
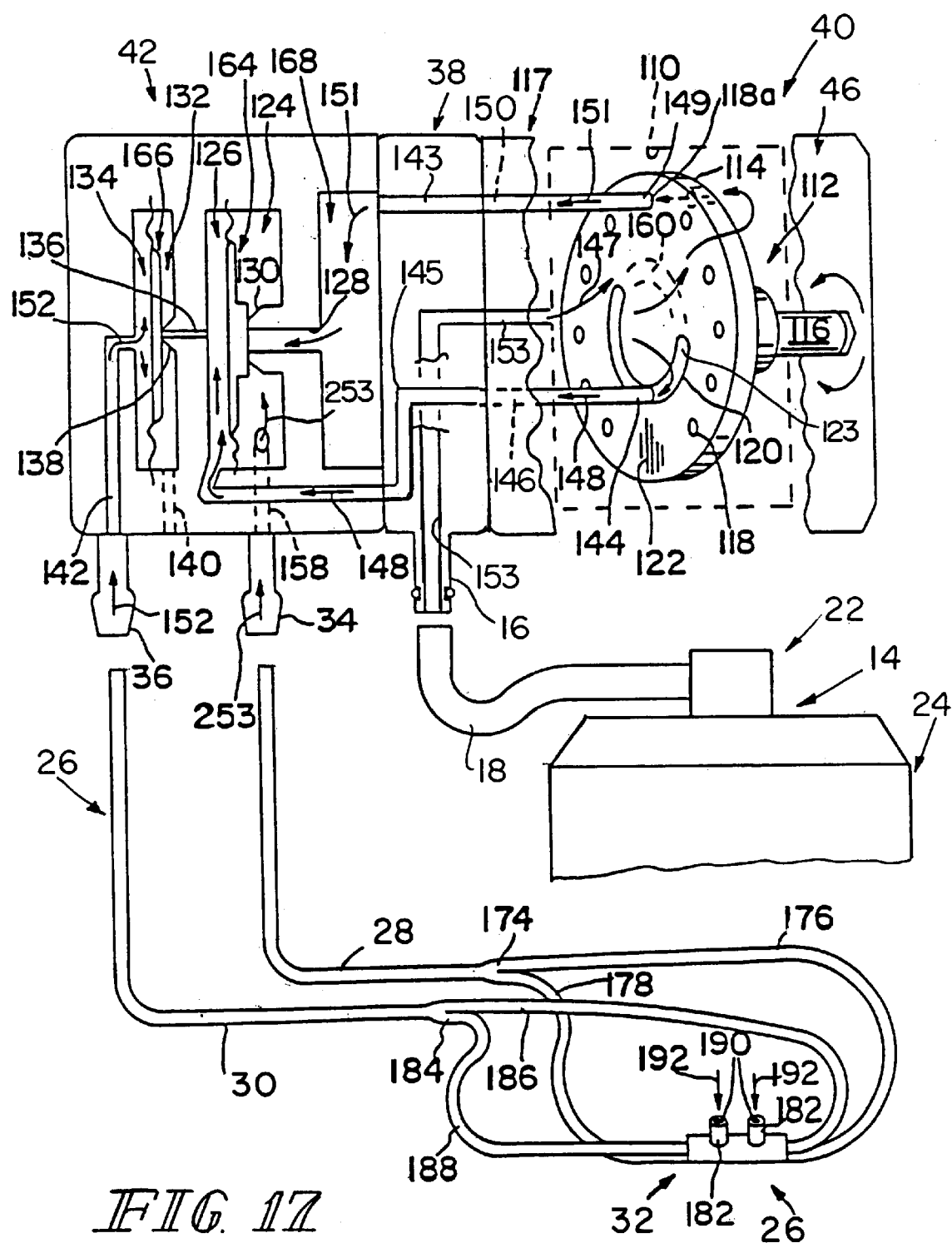
FIG. 17 is a schematic view of the assembly of FIG. 12.
Figure 18:
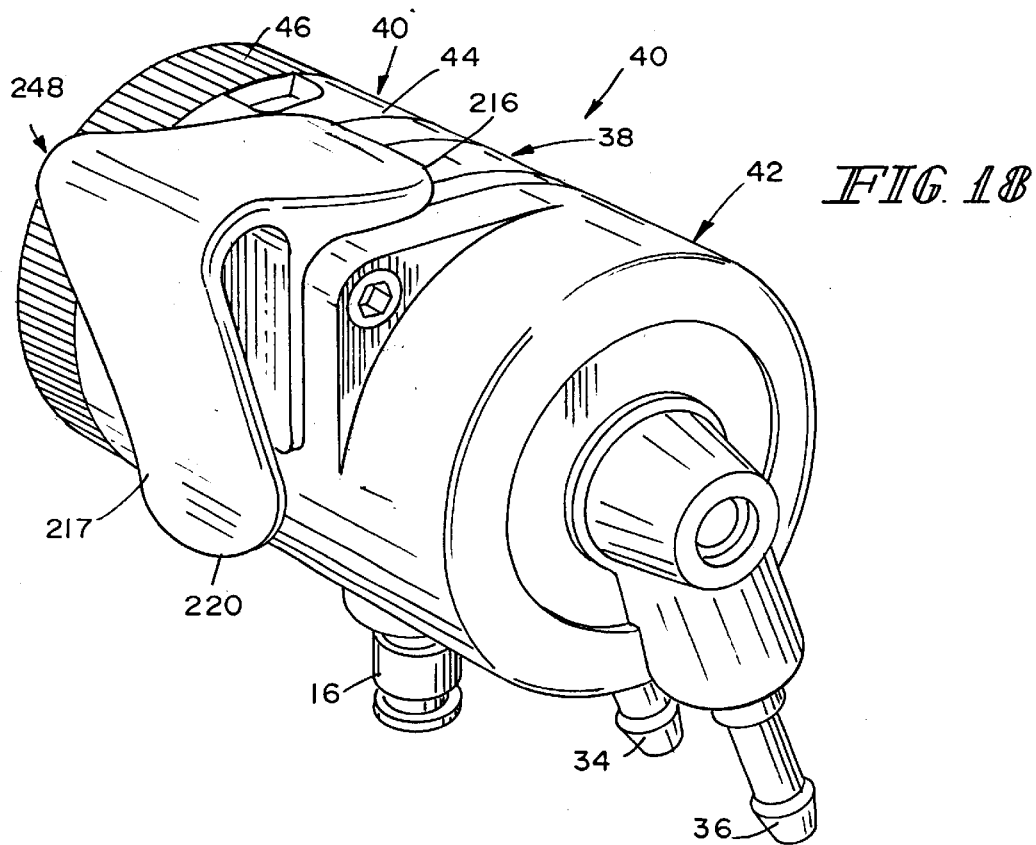
FIG. 18 is a perspective view of the portable oxygen meter of FIG. 2 carrying a belt clip.
Figure 19:
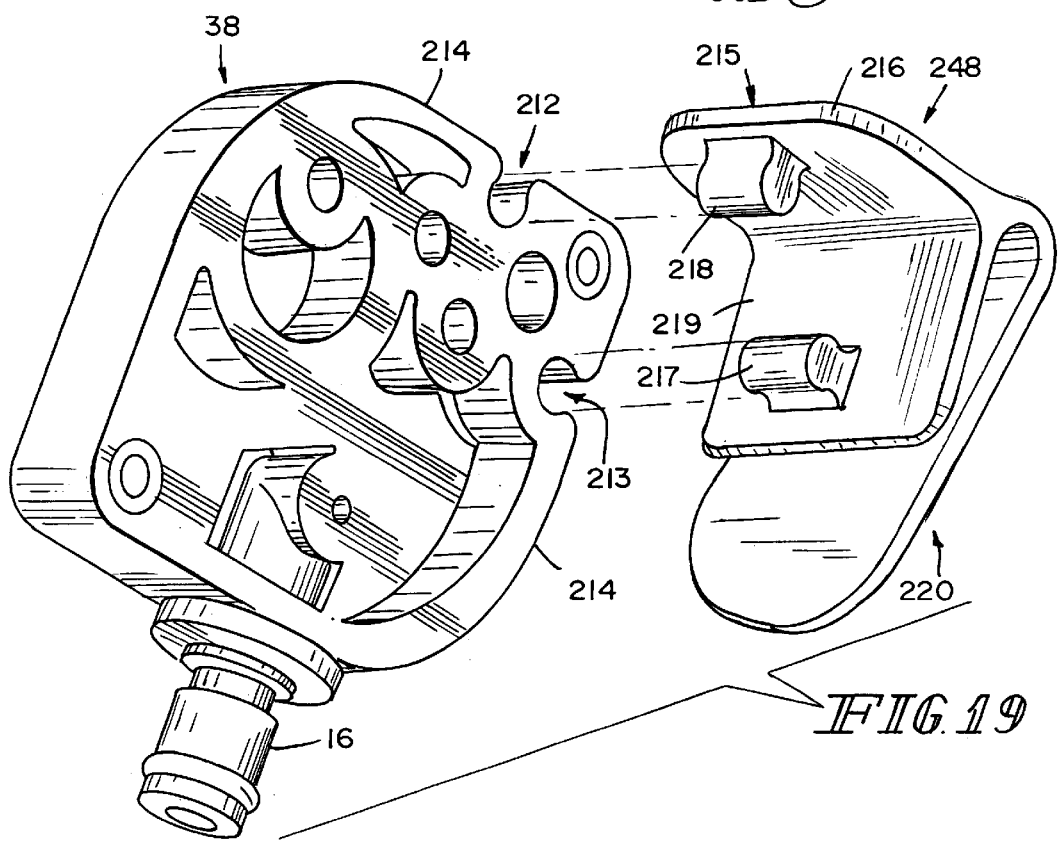
FIG. 19 is a perspective view of a manifold and the belt clip in the portable oxygen meter of FIG. 18 and a pair of lugs appended to a mounting flange of the belt clip and arranged to mount in lug-receiving notches formed in the manifold.
Figure 20:
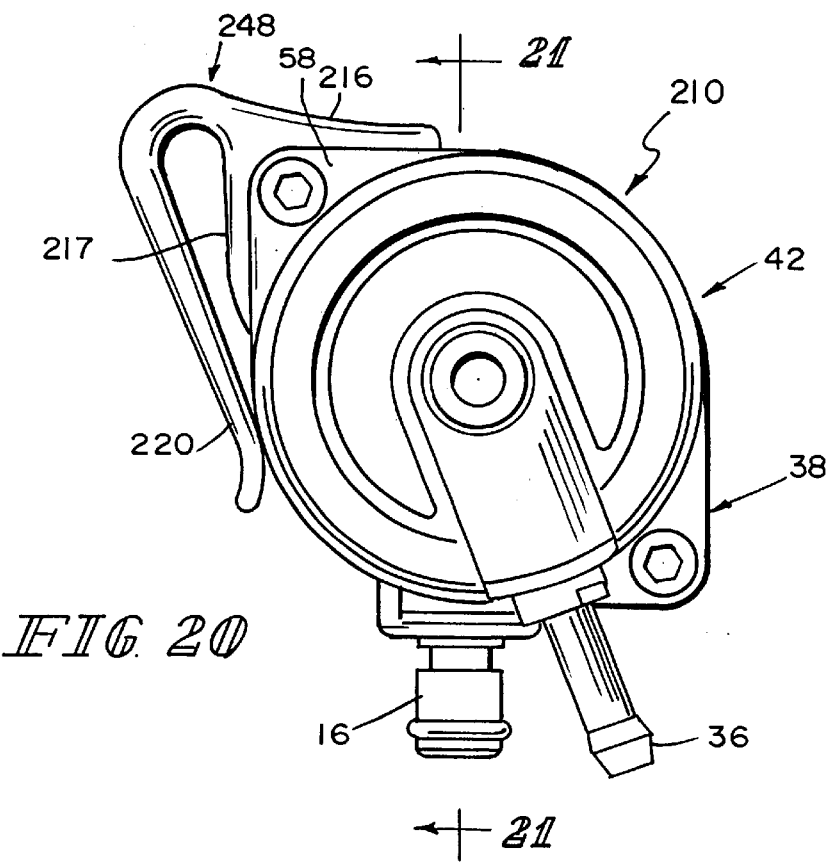
FIG. 20 is an end view of the portable oxygen meter of FIG. 18.
Figure 21:
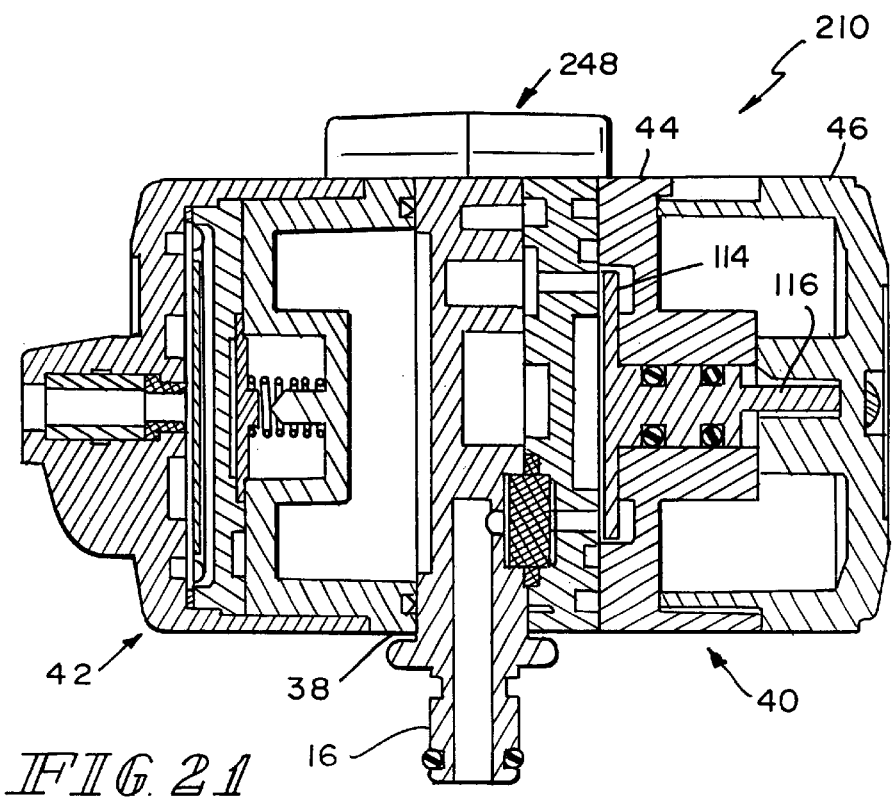
FIG. 21 is a sectional view taken along line 21—21 of FIG. 20 showing an internal configuration of the portable oxygen meter of FIGS. 18 and 20.

Oxygen delivery system 211 is shown diagrammatically in FIG. 12 and illustratively in FIG. 1. Portable oxygen meter 10 includes manifold 38, flow controller 40, and pneumatic demand oxygen conserver 42. A mount 13 is used to couple portable oxygen meter 10 to patient 12 or an article of clothing on patient 12. Manifold 38 is formed to include an inlet conduit 153 configured to conduct low-pressure oxygen from low-pressure oxygen inlet 16 into flow controller 40. Manifold 38 is also formed to include a patient supply passageway 143 and a diaphragm supply passageway 145 configured to conduct low-pressure oxygen from flow controller 40 to oxygen conserver 42. A preferred embodiment of the oxygen meter 10 included in oxygen delivery system 211 is shown in FIG. 17 and described below. A low-pressure, liquid oxygen tank 20 (shown in FIG. 1A) could be coupled to oxygen supply tube 18 as a replacement for high-pressure oxygen tank 24 and pressure regulator 22.

Figure 13:
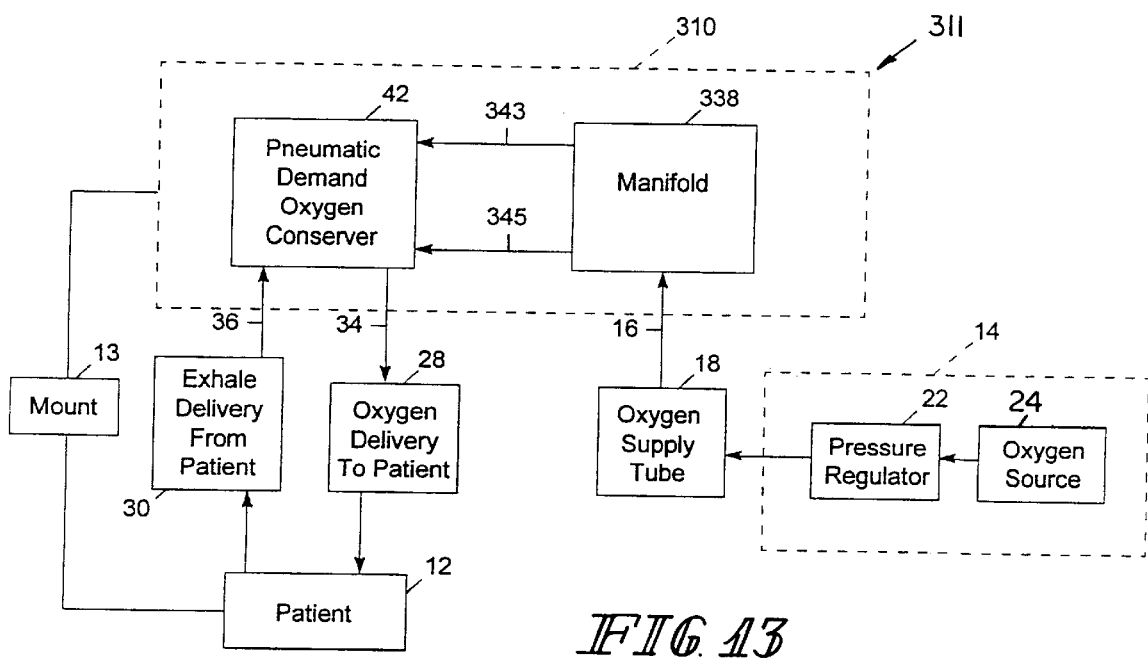
FIG. 13 is a diagrammatic view of another oxygen delivery system in accordance with the present invention showing an oxygen supply tube coupled to a manifold included in an oxygen meter having a pneumatic demand oxygen conserver.

Another oxygen delivery system 311 is shown diagrammatically in FIG. 13. Portable oxygen meter 310 includes manifold 338 and pneumatic demand oxygen conserver 42. A mount 13 is used to couple portable oxygen meter 310 to patient 12 or an article of clothing on patient 12. Manifold 338 is formed to include means for receiving a flow of low-pressure oxygen through low-pressure oxygen inlet 16 and splitting that oxygen flow so that some of the oxygen flows to oxygen conserver 42 through patient supply passageway 343 at a selected flow rate and some of the oxygen flows to oxygen conserver 42 through a diaphragm supply passageway 345. An embodiment of a pneumatic demand oxygen conserver 42 suitable for use in oxygen delivery system 311 is shown in FIG. 17. A low-pressure, liquid oxygen tank 20 (shown in FIG. 1A) could be coupled to oxygen supply tube 18 as a replacement for high-pressure oxygen 24 and pressure regulator 22.

Figure 14:
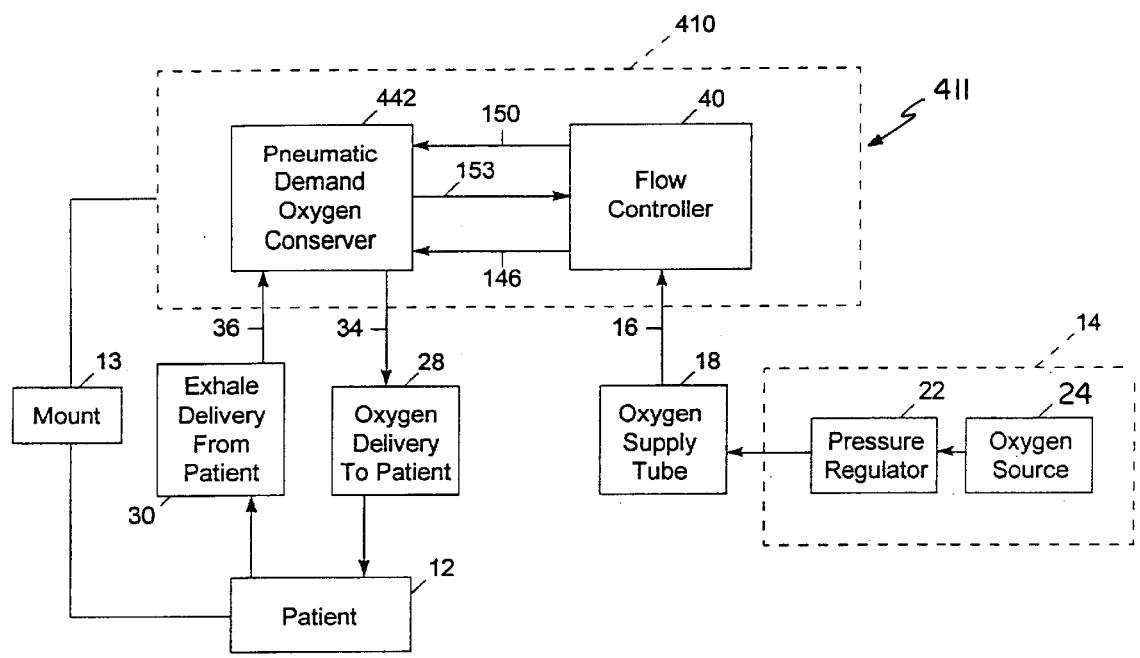
FIG. 14 is a diagrammatic view of yet another oxygen delivery system in accordance with the present invention showing an oxygen supply tube coupled to an oxygen meter having a pneumatic demand oxygen conserver and a flow controller.

Another oxygen delivery system 411 is shown diagrammatically in FIG. 14. Portable oxygen meter 410 includes pneumatic demand oxygen conserver 442 and flow controller 40. A mount 13 is used to couple portable oxygen meter 410 to patient 12 or an article of clothing worn by patient 12. Oxygen conserver 442 is similar to oxygen conserver 42 except that conserver 442 is formed to include low-pressure oxygen inlet 16 and an inlet conduit 153 configured to conduct low-pressure oxygen to flow controller 40. Flow controller 40 is configured to discharge a first flow of low-pressure oxygen to a diaphragm valve member (like 164 in FIG. 17) in oxygen conserver 442 through first outlet means 146 and a second flow of low-pressure oxygen to a patient through second outlet means 150. An embodiment of a flow controller 40 suitable for use in oxygen delivery system 411 is shown in FIG. 17. A low-pressure liquid oxygen tank 20 (shown in FIG. 1A) could be coupled to oxygen supply tube 18 as a replacement for high-pressure oxygen tank 24 and pressure regulator 22.

Figure 15:
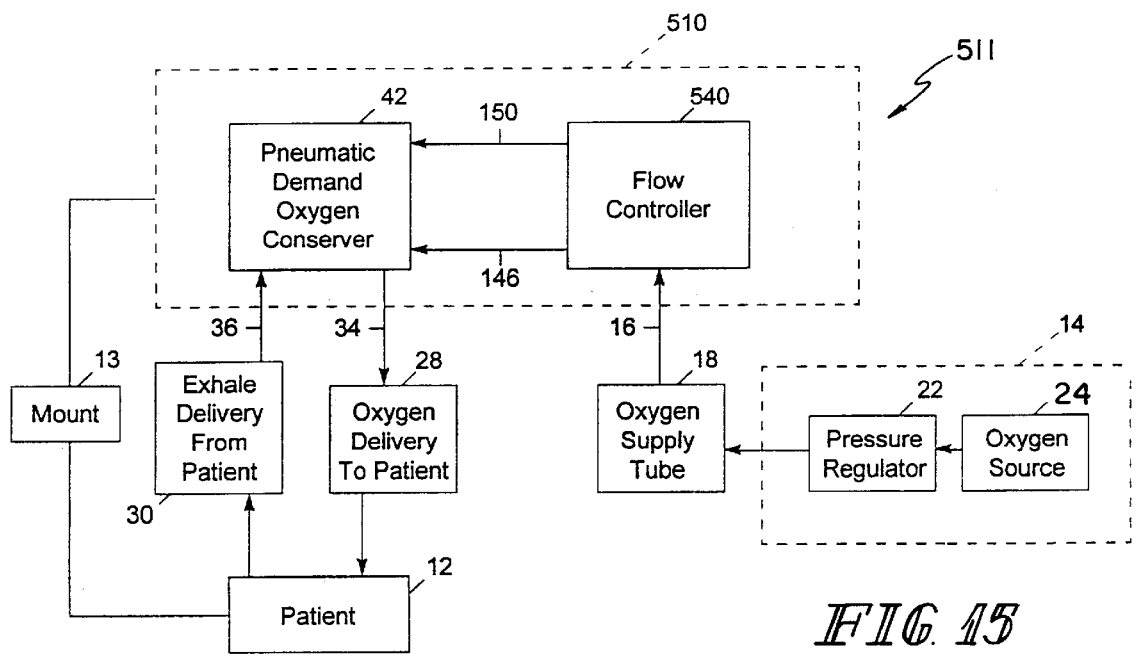
FIG. 15 is a diagrammatic view of still another oxygen delivery system in accordance with the present invention showing an oxygen supply tube coupled to a flow controller in an oxygen meter having a pneumatic demand oxygen conserver and a flow controller.

Still another oxygen delivery system 511 is shown diagrammatically in FIG. 15. Portable oxygen meter 510 includes pneumatic demand oxygen conserver 42 and flow controller 540. A mount 13 is used to couple portable oxygen meter 510 to patient 12 or an article of clothing worn by patient 12. Flow controller 540 is similar to flow controller 40 except that flow controller 540 is formed to include low-pressure oxygen inlet 16. Flow controller 40 is configured to discharge a first flow of low-pressure oxygen to a diaphragm valve member (like 164 in FIG. 17) in oxygen conserver 42 through first outlet means 146 and a second flow of low-pressure oxygen to a patient through second outlet means 150. An embodiment of an oxygen conserver suitable for use in oxygen delivery system 511 is shown in FIG. 17. A low-pressure liquid oxygen tank 20 (shown in FIG. 1A) could be coupled to oxygen supply tube 18 as a replacement for high-pressure oxygen tank 24 and pressure regulator 22.

Figure 16:
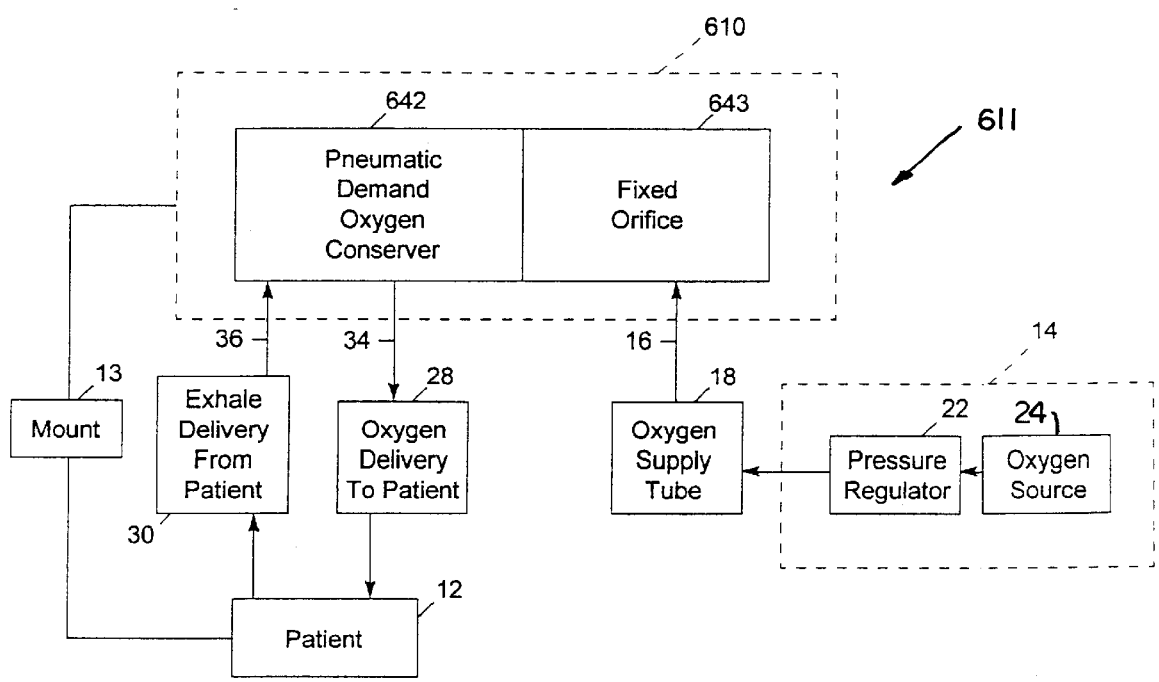
FIG. 16 is a diagrammatic view of an additional oxygen delivery system in accordance with the present invention showing an oxygen meter comprising a pneumatic demand oxygen conserver provided with a fixed orifice and an oxygen supply tube coupled to the fixed orifice.

Yet another oxygen delivery system 611 including a mount 13 is shown diagrammatically in FIG. 16. Portable oxygen meter 610 includes a pneumatic demand oxygen conserver 642 that is formed to include a fixed orifice 643 coupled in fluid communication to low-pressure oxygen inlet 16. Fixed orifice 643 is sized to establish the flow rate of low-pressure oxygen passing to oxygen conserver 642. Fixed orifice 643 can be a modular unit that is configured to be mounted in and removed from oxygen conserver 642 by a dealer or a technician to enable the size of fixed orifice to be changed. Oxygen conserver 642 is similar to oxygen conserver 42 shown in FIG. 17 except that low-pressure oxygen is admitted through fixed orifice 643 rather than manifold 38. Oxygen conserver 642 is formed to include means for splitting the oxygen flow admitted through fixed orifice 643 into a first flow of low-pressure oxygen that is conducted to a diaphragm valve member (like 164 in FIG. 17) and a second flow of low-pressure oxygen that is conducted to a patient through oxygen outlet 34. A low-pressure liquid oxygen tank 20 (shown in FIG. 1A) could be coupled to oxygen supply tube 18 as a replacement for high-pressure oxygen tank 24 and pressure regulator 22.

A diagrammatic illustration of a preferred embodiment of a modular oxygen meter 10 is provided in FIG. 17 to show how oxygen meter 10 can be operated to control the flow of low-pressure oxygen gas from flexible supply line 18 to a patient 12 wearing and using a breathing cannula 26. Oxygen meter 10 can function in "demand" mode to deliver oxygen to a patient 12 only when the patient breathing through cannula 26 is inhaling and in "continuous" mode to deliver oxygen continuously to the patient 12 whether the patient is inhaling through or exhaling into cannula 26. Oxygen meter 10 can be set in an "off" mode so that no oxygen gas is flowing from supply line 18 to cannula 26 through oxygen meter 10.

FIG. 17 shows how air exhaled by a patient into nasal cannula 26 is transmitted through sensing port 36 to oxygen conserver 42 and how a lack of air inhalation by the patient causes a diaphragm valve member 164 and an inhale/exhale sensing diaphragm 166 positioned in oxygen conserver 42 to cooperate to block flow of oxygen passing through a patient supply passageway 143 formed in manifold 38 and an oxygen supply chamber 168 formed in oxygen conserver 42 from oxygen conserver 42 into nasal cannula 26. The inhale/exhale sensing diaphragm 166 is configured to move to an actuated position whenever a patient 12 breathing through nasal cannula 26 inhales to allow pressurized oxygen in oxygen supply chamber 168 in oxygen conserver 42 to assist in moving diaphragm valve member 164 to a venting position so that oxygen is discharged from oxygen conserver 42 into nasal cannula 26 through low-pressure oxygen outlet 34.

Dual lumen cannula 26 is shown diagrammatically in FIG. 17. Cannula 26 includes a flexible gas supply tube 28 and a breath sensor tube 30. Gas supply tube 28 is coupled to oxygen outlet 34 on oxygen conserver 42 and adjacent to the patient divides at juncture 174 to present two branch legs 176, 178. These branch legs 176, 178 are interconnected by means of a nasal delivery structure 32 including a pair of spaced-apart gas delivery tubes 182 insertable into the nasal cavities of a patient. Breath sensor tube 30 is coupled to sensor port 36 on oxygen conserver 42 and adjacent to the patient divides at juncture 184 to present two branch legs 186, 188. A pair of short sensor tubes 190 are located within the spaced-apart gas delivery tubes 182 and coupled to branch legs 186, 188. The function of breath sensor tube 30 is to convey and transmit via short sensor tubes 190 the pressure conditions induced during the patient's breathing efforts, such pressure conditions being transmitted to inhale/exhale sensing diaphragm 166 in oxygen conserver 42 via sensor port 36.

Referring now to FIG. 17, oxygen meter 10 is shown in demand mode during patient exhaling. Breath exhaled by the patient wearing nasal cannula 26 into the two short sending tubes 190 provided in nasal delivery structure 32 is represented diagrammatically by two downwardly pointing arrows 192.

Pressure regulator 22 is configured to include a conventional internal regulator mechanism coupled to low-pressure oxygen inlet 16 on portable oxygen meter 10 by flexible supply tube 18. In many cases, pressure regulator 22 will be mounted on top of an oxygen tank 24. Pressure regulator 22 operates in a conventional manner to convert high pressure (e.g., 3,000 psi) oxygen gas into low pressure (e.g., 20 or 50 psi) oxygen suitable for use in flow controller 40 and oxygen conserver 42 and by the patient wearing nasal cannula 26. In a presently preferred embodiment, a low-pressure, liquid oxygen tank 20, as shown in FIG. 1A, is coupled to flexible supply tube 18 instead of a pressure regulator 22 mounted on top of a high-pressure oxygen tank 24.

Flow controller 40 is formed to include a sealed internal chamber 110 coupled to inlet conduit 153 and first and second outlet means 146, 150. Low-pressure oxygen discharged from flexible supply tube 18 is admitted into internal chamber 110 in flow controller 40 via inlet conduit 153 formed in manifold 38 and flow controller 40 as shown in FIG. 17. A rotary valve 112 included in flow controller 40 includes a rotor disk 114 positioned to lie in internal chamber 110 and a drive shaft 116 fixed to rotor disk 114 and coupled to rotate with flow selector knob 46 relative to base 117. The rotor disk 114 is formed to include various oxygen flow-metering apertures 118, an oxygen flow channel 120, and a flow-shutoff plate 122. Rotary valve 112 is positioned to be moved between a first position range shown, for example, in FIG. 17 and other positions (not shown) to regulate flow of oxygen from flow controller 40 to oxygen conserver 42. Reference is made to U.S. Application Ser. No. 08/849,417 (U.S. counterpart to PCT/US96/15549, filed on Sep. 27, 1996 and published as WO97/11734 on Apr. 3, 1997), which is incorporated by reference herein, for a detailed description of rotary valve 112 and the configuration and operation of nasal cannula 26, flow controller 40, and oxygen conserver 42. Reference is also made to U.S. Pat. No. 5,360,000, which is incorporated by reference herein, for descriptions of pneumatic demand oxygen conservers.

Oxygen conserver 42 is formed to include an oxygen flow chamber 124 on one side of diaphragm valve member 164 and a diaphragm biasing chamber 126 on the other side of diaphragm valve member 164. A central passage 128 conducts pressurized oxygen from oxygen supply chamber 168 into oxygen flow chamber 124 for delivery to oxygen outlet 34 (and cannula 26) whenever diaphragm valve member 164 is moved to disengage a valve seat 130 around central passage 128. Oxygen conserver 42 also includes a vent chamber 132 on one side of inhale/exhale sensing diaphragm 166 and a venting control chamber 134 on the other side of inhale/exhale sensing diaphragm 166. A central passage 136 conducts pressurized oxygen from diaphragm biasing chamber 126 into vent chamber 132 for discharge to the atmosphere through vent passageway 140 whenever inhale/exhale sensing diaphragm 166 is moved to disengage a valve seat 138 around central passage 136. A breath conduit 142 interconnects oxygen sensor port 36 and venting control chamber 134 in fluid communication so that a vacuum is applied to venting control chamber 134 via nasal cannula 26, oxygen sensor port 36, and breath conduit 142 whenever a patient breathing through nasal cannula 26 inhales.

To place portable oxygen meter 10 in demand mode, the user turns flow selector knob 46 in flow controller 40 to place rotary valve 112 in a first position range so as to cause inlet 144 of first outlet means 146 to communicate with oxygen flow channel 120 formed in rotor disk 114 and inlet 149 of second outlet means 150 to communicate with one of the oxygen flow-metering apertures 118 formed in rotor disk 114 as shown in FIG. 17. When in demand mode, portable oxygen meter 10 operates to supply oxygen to the patient breathing through nasal cannula 26 only when the patient inhales.

As shown in FIG. 17, low-pressure oxygen 147 discharged from manifold 38 into flow controller 40 is split into two flow streams in sealed internal chamber 110 by rotor disk 114 when rotary valve 112 is in the first position range so that one stream of oxygen 148 is discharged from flow controller 40 into a diaphragm supply passageway 145 formed in manifold 38 and another stream of oxygen 151 is discharged from flow controller 40 into patient supply passageway 143 formed in manifold 38. As shown diagrammatically in FIG. 17, the one oxygen stream 148 flows from internal chamber 110 into inlet 144 of first outlet means 146 after gaining access to the open mouth of inlet 144 by first passing through a portion of oxygen flow channel 120 formed in rotor disk 114. Simultaneously, the other oxygen stream 151 flows from internal chamber 110 through a selected oxygen flow-metering aperture 118a formed in rotor disk 114 into inlet 149 of second outlet means 150.

As shown in FIG. 17, diaphragm valve member 164 in oxygen conserver 42 is retained in a closed position engaging valve seat 130 to block flow of oxygen from oxygen supply chamber 168 through central passage 128 into oxygen flow chamber 124 whenever a patient wearing nasal cannula 26 is not inhaling. By exhaling, the patient discharges exhaled air 152 through gas delivery tubes 182 in nasal delivery structure 32, branch legs 186, 188, sensor tube 30, sensor port 36, and breath conduit 142 to pressurize venting control chamber 134 in oxygen conserver 42 and help retain inhale-exhale sensing diaphragm 166 in a closed position engaging valve seat 138 to close central passage 136. Simultaneously, the first stream of oxygen 148 discharged from flow controller 40 passes through diaphragm supply passageway 145 to reach diaphragm biasing chamber 126 and urge diaphragm valve member 164 to a closed position engaging valve seat 130 to close central passage 128. When central passage 128 is closed, pressurized oxygen is unable to pass from oxygen supply chamber 168 out of oxygen conserver 42 through oxygen outlet 34. Even though exhaling air 253 from a patient is passing through oxygen outlet 34 into oxygen flow chamber 124, the pressure of the exhaled air 253 in chamber 124 acting on the right side of diaphragm valve member 164 does not generate a force that is great enough to move diaphragm valve member 164 from its closed position.

Diaphragm valve member 164 can be moved (to the left in FIG. 17) to an opened position (not shown) to allow oxygen 151 to flow to a patient wearing nasal cannula 26 from oxygen supply chamber 168 in oxygen conserver 42 through central passage 128, oxygen flow chamber 124, oxygen discharge channel 158, oxygen outlet 34, gas supply tube 28, leg branches 176, 178, and gas delivery tubes 182 in nasal delivery structure 32. By inhaling, the patient draws air out of venting control chamber 134 through breath conduit 142, sensor port 36, sensor tube 30, branch legs 186, 188, and nasal delivery structure 32. Diaphragm valve member 164 is able to move to an opened position because pressurized oxygen extant in diaphragm biasing chamber 126 is discharged to the atmosphere through central passage 136, vent chamber 132 (opened to central passage 136), and vent passageway 140.

To place portable oxygen meter 10 in continuous mode, the user turns flow selector knob 46 (about its axis of rotation relative to base 117) to place rotary valve 112 in a second position range (not shown) so as to cause inlet 144 of first outlet means 146 to engage only a flat wall portion 160 (extending between opposite ends 121, 123 of oxygen flow channel 120) of rotor disk 114 so that inlet 144 does not communicate with the C-shaped oxygen flow channel 120 formed in rotor disk 114. When rotor disk 114 is in this position, no oxygen is able to flow out of internal chamber 110 formed in flow controller 40 into diaphragm supply passageway 145 to reach diaphragm biasing chamber 126 because inlet 144 sealingly engages flat wall portion 160 of rotor disk 114. As a result, there is insufficient oxygen pressure extent in diaphragm biasing chamber 126 to act on the diaphragm valve member 164 and generate a force sufficient to move diaphragm valve member 164 to a closed position and thus diaphragm valve member 164 remains open continuously to allow continuous oxygen flow from oxygen supply chamber 168 in oxygen conserver 42 to a patient breathing through cannula 26 via central passage 128, oxygen flow chamber 124, oxygen discharge channel 158, oxygen outlet 34, and nasal cannula 26.

To place portable oxygen meter 10 in off mode, the user turns flow selector knob 46 (about its axis of rotation relative to base 117) in flow controller 40 to place rotary valve 112 in a third position range (not shown) so as to cause (1) inlet 144 of first outlet means 146 to engage only flat wall portion 160 of rotor disk 114 so that inlet 144 does not communicate with the C-shaped oxygen flow channel 120 formed in rotor disk 114 (and hence oxygen extant in chamber 110) and (2) inlet 149 of second outlet means 150 to engage only flow-shutoff plate 122 on rotor disk 114 so that inlet 149 does not communicate with any one of the oxygen flow-metering apertures 118 formed in rotor disk 114. As a result, no oxygen is discharged from internal chamber 110 in flow controller 40 through the diaphragm and patient supply passageways 145, 143 formed in manifold 38 toward the oxygen conserver 42 and the portable oxygen meter 10 is inactive.

Although the invention has been described in detail with reference to preferred embodiments, variations and modifications exist within the scope and spirit of the invention as described and defined in the following claims.

What is claimed is:

1. An oxygen-delivery system comprising
   a portable oxygen meter including a low-pressure oxygen inlet, a low-pressure oxygen outlet, and an exhale-inhale sensing port,
   an oxygen-supply source including a discharge outlet and configured to discharge low-pressure oxygen through the discharge outlet,
   a flexible supply tube having an inlet end coupled to the discharge outlet of the oxygen supply source and an outlet end coupled to the low-pressure oxygen inlet of the portable oxygen meter to conduct low-pressure oxygen from the oxygen-supply source into the portable oxygen meter through the low-pressure oxygen inlet,
   a nasal cannula coupled to the low-pressure oxygen outlet and the exhale-inhale sensing port and adapted to be inserted into the nasal cavities of a patient, the portable oxygen meter further including a pneumatic demand oxygen conserver including a diaphragm valve member movable between a flow-delivery position allowing flow of low-pressure oxygen from the low-pressure oxygen inlet to the low-pressure oxygen outlet and a flow-blocking position blocking flow of low-pressure oxygen from the low-pressure oxygen inlet to the low-pressure oxygen outlet, control means coupled to the exhale-inhale sensing port for causing the diaphragm valve member to move to the flow-delivery position in response to inhalation of the patient breathing through the nasal cannula and to move to the flow-blocking position in response to a lack of inhalation by the patient during exhalation through the nasal cannula, and an oxygen flow passage located between the low-pressure oxygen inlet and the diaphragm valve member and arranged to pass low-pressure oxygen through an oxygen flow-metering aperture having a predetermined internal diameter to meter low-pressure oxygen flowing in the portable oxygen meter from the low-pressure oxygen inlet to the low-pressure oxygen outlet at a selected oxygen flow rate, and
   a mount including a flange coupled to the portable oxygen meter and a clip adapted to be coupled to an item of clothing worn by the patient.

2. The oxygen-delivery system of claim 1, wherein the portable oxygen meter further includes a manifold formed to include the low-pressure oxygen inlet and a flow controller formed to include the oxygen flow passage.

3. The oxygen-delivery system of claim 1, wherein the portable oxygen meter further includes a manifold formed to include the low-pressure oxygen inlet and coupled to this pneumatic demand oxygen conserver.

4. The oxygen-delivery system of claim 3, wherein the manifold is formed to include means for receiving a flow of low-pressure oxygen through the low-pressure oxygen inlet and splitting the flow of low-pressure oxygen so that some of the low-pressure oxygen flows to one side of the diaphragm valve member through a patient supply passageway formed in the manifold and the pneumatic demand oxygen conserver at selected flow rate and some of the oxygen flows to an opposite side of the diaphragm valve member through a diaphragm valve supply passageway formed in the manifold and the pneumatic demand oxygen conserver.

5. The oxygen-delivery system of claim 1, wherein the pneumatic demand oxygen conserver is formed to include the low-pressure oxygen inlet.

6. The oxygen-delivery system of claim 5, wherein the portable oxygen meter further includes a flow controller formed to include the oxygen flow passage and the pneumatic demand oxygen conserver is formed to include an inlet conduit configured to conduct low-pressure oxygen from the low-pressure oxygen inlet to the flow controller on route to the oxygen flow passage in the flow controller.

7. The oxygen-delivery system of claim 1, wherein the portable oxygen meter further includes a flow controller formed to include the oxygen flow passage, the low-pressure oxygen inlet, and a conduit configured to conduct low-pressure oxygen from the low-pressure oxygen inlet to the oxygen flow passage.

8. The oxygen-delivery system of claim 1, wherein the pneumatic demand oxygen conserver is formed to include the low-pressure oxygen inlet and the oxygen flow passage.

9. An oxygen-delivery system comprising
   a portable oxygen meter including a low-pressure oxygen inlet, a low-pressure oxygen outlet, and an exhale-inhale sensing port,
   an oxygen-supply source including a discharge outlet and configured to discharge low-pressure oxygen through the discharge outlet,
   a flexible supply tube having an inlet end coupled to the discharge outlet of the oxygen supply source and an outlet end coupled to the low-pressure oxygen inlet of the portable oxygen meter to conduct low-pressure oxygen from the oxygen-supply source into the portable oxygen meter through the low-pressure oxygen inlet,
   a nasal cannula coupled to the low-pressure oxygen outlet and the exhale-inhale sensing port and adapted to be inserted into the nasal cavities of a patient, the portable oxygen meter further including a pneumatic demand oxygen conserver including a diaphragm valve member movable between a flow-delivery position allowing flow of low-pressure oxygen from the low-pressure oxygen inlet to the low-pressure oxygen outlet and a flow-blocking position blocking flow of low-pressure oxygen from the low-pressure oxygen inlet to the low-pressure oxygen outlet, control means coupled to the exhale-inhale sensing port for causing the diaphragm valve member to move to the flow-delivery position in response to inhalation of the patient breathing through the nasal cannula and to move to the flow-blocking position in response to a lack of inhalation by the patient during exhalation through the nasal cannula, and an oxygen flow passage located between the low-pressure oxygen inlet and the diaphragm valve member and arranged to pass low-pressure oxygen through an oxygen flow-metering aperture having a predetermined internal diameter to meter low-pressure oxygen flowing in the portable oxygen meter from the low-pressure oxygen inlet to the low-pressure oxygen outlet at a selected oxygen flow rate, the portable oxygen meter further including a manifold formed to include the low-pressure oxygen inlet and at least one lug-receiving notch, and a meter mount including a mounting flange extending into the at least one lug-receiving notch formed in the manifold and a clip fixed to the mounting flange and adapted to be coupled to an item of clothing worn by the patient breathing through the nasal cannula.

10. The oxygen-delivery system of claim 9, wherein the manifold is formed to include first and second lug-receiving notches and the mounting flange includes a top wall carrying a first lug placed in the first lug-receiving notch and a side wall carrying a second lug placed in the second lug-receiving notch.

11. The oxygen-delivery system of claim 10, wherein the side wall is oriented to lie in about perpendicular relation to the top wall.

12. An oxygen-delivery system comprising a portable oxygen meter including a low-pressure oxygen inlet, a low-pressure oxygen outlet, and an exhale-inhale sensing port, an oxygen-supply source including a discharge outlet and configured to discharge low-pressure oxygen through the discharge outlet, a flexible supply tube having an inlet end coupled to the discharge outlet of the oxygen supply source and an outlet end coupled to the low-pressure oxygen inlet of the portable oxygen meter to conduct low-pressure oxygen from the oxygen-supply source into the portable oxygen meter through the low-pressure oxygen inlet, and a nasal cannula coupled to the low-pressure oxygen outlet and the exhale-inhale sensing port and adapted to be inserted into the nasal cavities of a patient, the portable oxygen meter being configured to provide low-pressure oxygen provided by the oxygen-supply source without signal and delivery distortion for delivery to the patient upon inhalation of the patient when the portable oxygen meter is spaced at least 15 feet to over 20 feet away from the oxygen-supply source to promote mobility of the patient, the portable oxygen meter further including a pneumatic demand oxygen conserver including a diaphragm valve member movable between a flow-delivery position allowing flow of low-pressure oxygen from the low-pressure oxygen inlet to the low-pressure oxygen outlet and a flow-blocking position blocking flow of low-pressure oxygen from the low-pressure oxygen inlet to the low-pressure oxygen outlet, control means coupled to the exhale-inhale sensing port for causing the diaphragm valve member to move to the flow-delivery position in response to inhalation of the patient breathing through the nasal cannula and to move to the flow-blocking position in response to a lack of inhalation by the patient during exhalation through the nasal cannula, and an oxygen flow passage located between the low-pressure oxygen inlet and the diaphragm valve member and arranged to pass low-pressure oxygen through an oxygen flow-metering aperture having a predetermined internal diameter to meter low-pressure oxygen flowing in the portable oxygen meter from the low-pressure oxygen inlet to the low-pressure oxygen outlet at a selected oxygen flow rate.

13. The oxygen-delivery system of claim 12, wherein the flexible supply tube has a length of at least 15 feet to over 20 feet away.

14. The oxygen-delivery system of claim 12, wherein the portable oxygen meter is configured to provide low-pressure oxygen provided by the oxygen-supply source without signal and delivery distortion for delivery to the patient upon inhalation of the patient when the portable oxygen meter is spaced at least 50 feet away from the oxygen-supply source to promote mobility of the patient.

15. The oxygen-delivery system of claim 12, further comprising a mount configured to be coupled to the portable oxygen meter to mount the portable oxygen meter away from the oxygen-supply source.

16. The oxygen-delivery system of claim 15, wherein the mount includes a belt clip including a connector coupled to the portable oxygen meter and clip hardware fixed to the connector and arranged to hook onto a belt worn by the patient.

17. The oxygen-delivery system of claim 15, wherein the portable oxygen meter is formed to include lug-receiving notches, the mount includes a mounting flange and a clip appended to the mounting flange and arranged to hook onto a belt worn by the patient, and the mounting flange includes a top wall carrying a first lug sized to fit into a first of the lug-receiving notches and a side wall carrying a second lug sized to fit into a second of the lug-receiving notches.

18. The oxygen-delivery system of claim 15, wherein the mount includes a strap wrapped around a portion of the portable oxygen meter, a hook-and-loop connector, and a clasp adapted to hook onto a belt worn by the patient and the hook-and-loop connector includes a first portion fixed to the strap and a second portion fixed to the clasp and configured to mate with the first portion.

19. The oxygen-delivery system of claim 15, wherein the mount includes a sheet sized to fit into a pocket formed on a piece of clothing worn by the patient and a flap appended to the sheet and arranged to lie in front of the pocket and carry the portable oxygen meter thereon.

20. The oxygen-delivery system of claim 15, wherein the mount includes a plate adapted to fit between a first part of furniture and a second part of the furniture spaced apart from the first part and a flange appended to the plate and arranged to hang downwardly in front of the first part and the portable oxygen meter is coupled to the flange so that the portable oxygen meter can be coupled to the furniture.

21. The oxygen-delivery system of claim 15, wherein the mount includes a clamp adapted to couple to a fixture and a support coupled to the clamp and the portable oxygen meter so that the portable oxygen meter can be coupled to the fixture.

22. The oxygen-delivery system of claim 15, wherein the mount includes a sleeve wrapped around the portable oxygen meter and formed to include windows therein to view and expose portions of the portable oxygen meter, support straps coupled to the sleeve, and rings and each ring is coupled to one of the support straps and adapted to be coupled to an article worn by the patient to hang the sleeve from the article.

23. The oxygen-delivery system of claim 15, wherein the mount includes a clip coupled to the portable oxygen meter and an anchor adapted to be placed on a base, the anchor includes a first segment, a second segment arranged in series with the first segment, and a hinge interconnecting the first segment and the second segment, and one of the first and second segments includes a pocket sized to receive the clip so that the portable oxygen meter can be coupled to the base.

24. The oxygen-delivery system of claim 15, wherein the mount includes a base formed to include a channel sized to receive the portable oxygen meter and a friction pad adhered to an underside of the base and adapted to be placed on a surface so that the portable oxygen meter can be supported above the surface.

25. The oxygen-delivery system of claim 24, wherein the mount further includes a handle appended to the base to enable the patient to move the mount.

26. The oxygen-delivery system of claim 15, wherein the mount includes a clip coupled to the portable oxygen meter, a base, a friction pad adhered to an underside of the base and adapted to be placed on a surface, and an upright flange appended to the base and the clip engages the upright flange to support the portable oxygen meter above the surface.

* * * * *